United States Patent [19]
Kinet

[11] Patent Number: 6,165,799
[45] Date of Patent: Dec. 26, 2000

[54] DETECTION OF ANTI-FC$_\epsilon$R AUTOANTIBODIES IN ASTHMATICS

[75] Inventor: Jean-Pierre Kinet, Lexington, Mass.

[73] Assignee: Heska Corporation, Fort Collins, Colo.

[21] Appl. No.: 08/985,863

[22] Filed: Dec. 5, 1997

Related U.S. Application Data

[60] Provisional application No. 60/032,693, Dec. 10, 1996.

[51] Int. Cl.$^7$ .................................................. G01N 33/564
[52] U.S. Cl. ........................ 436/507; 435/7.24; 435/7.92; 435/29; 530/388.22; 530/389.6; 436/506
[58] Field of Search .................................... 436/506, 507, 436/536; 424/91; 435/7.1, 7.24, 7.9, 7.92, 29; 530/388.22, 387.1, 389.1, 389.6

[56] References Cited

FOREIGN PATENT DOCUMENTS

| | | |
|---|---|---|
| WO 91/12812 | 9/1991 | WIPO . |
| WO 92/18483 | 10/1992 | WIPO . |
| WO95/16203 | 6/1995 | WIPO . |
| WO 97/04125 | 2/1997 | WIPO . |
| WO 97/06440 | 2/1997 | WIPO . |

OTHER PUBLICATIONS

Adkinson, Is Asthma Always an Allergic Disease?, Trans Am Clin Climatol Assoc 103, 218–227, 1992.

Bigby, et al., Inflammation: Basic Principles and Clinical Correlates, Gallin JI, Goldstein IM, Synderman, R., Eds. (Raven Press, New York), pp. 889–906, 1992.

Bochner, et al., Immunological Aspects of Allergic Asthma, *Annu Rev Immunol* 12, 295–335, 1994.

Bonnefoy, et al., Receptors for IgE, *Curr Opin Immunol* 5, 944–949, 1993.

Burrows, et al., Association of Asthma with Serum IgE Levels and Skin–Test Reactivity to Allergens, *N Engl J Med* 320, 271–277, 1989.

Daeron, et al., Regulation of High–affinity IgE Receptor–Mediated Mast Cell Activation by Murine Low–Affinity IgE Receptors, *J Clin Invest* 95, 577–585, 1995.

Fiebiger, et al., Serum IgG Autoantibodies Directed Against the Alpha Chain of Fc$_\epsilon$RI: A Selective Marker and Pathogenetic Factor for a Distinct Subset of Chronic Urticaria Patients?, *J Clin Invest* 96, 2606–2612, 1995.

Grattan, et al., Detection of Circulating Histamine Releasing Autoantibodies with Functional Properties of Anti–IgE in Chronic Urticaria, *Clin Exp Allergy* 21, 695–704 1991.

Gruber, et al., Prevalence and Functional Role of Anti–IgE Autoantibodies in Urticaria Syndromes, *J Invest Dermatol* 90, 213–217, 1988.

Hide, et al., Autoantibodies Against the High–affinity IgE Receptor as a Cause of Histamine Release In Chronic Urticaria, *N Engl J Med* 328, 1599–1604, 1993.

MacGlashan, et al., Characteristics of Human Basophil Sulfidopeptide Leukotriene Release: Releasability Defined as the Ability of the Basophil to Respond to Dimeric Cross–Links, *J Immunol* 136, 2231–2239, 1986.

Marone, et al., IgG Anti–IgE from Atopic Dermatitis Induces Mediator Release from Basophils and Mast Cells, *J Invest Dermatol* 93, 246–252, 1989.

Martinez, et al., Asthma and Wheezing in the First Six Years of Life, *N Engl J Med* 332, 133–138, 1995.

McFadden, et al., Asthma, *N Engl J Med* 327, 1928–1937, 1992.

Niimi, et al., Dermal Mast Cell Activation by Autoantibodies Against the High–Affinity IgE Receptor in Chronic Urticaria, *J Invest Dermatol* 106, 1001–1006, 1996.

O'Hollaren, et al., Exposure to an Aeroallergen as a Possible Precipitating Factor in Respiratory Arrest in Young Patients with Asthma, *N Engl J Med* 324, 359–363, 1991.

Sears, et al., Relation Between Airway Responsiveness and Serum IgE in Children with Asthma and in Apparently Normal Children Transcellular Metabolism of Leukotrienes in the Lung, *N Engl J Med* 325, 1067–1071, 1991.

Tong, et al., Assessment of Autoimmunity in Patients with Chronic Urticaria, *Int Arch Allergy Immunol*, 99, 461–465, 1996.

Ochiai, et al., *Int Arch Allergy Immunol*, vol. 111 (supp 1), pp. 55–58, 1996.

Danoff et al., 1980, *J. Chron Dis,* vol. 33, No. 3, pp. 135–145.

Halpern, G.M., MD, 1991, *Allergie et Immunologie,* vol. 23, pp. 255–262.

Saban et al., *J. Allergy Clin Immunol,* vol. 94, No. 5, pp. 836–843. (1994).

Smith et al, 1995, *J Clin Pathol Mol Pathol,* vol. 48, pp. M145–M152.

*Primary Examiner*—Patrick Nolan
*Attorney, Agent, or Firm*—Heska Corporation

[57] ABSTRACT

The present invention includes a method to detect chronic pulmonary diseases of the airways associated with anti-Fc$_\epsilon$R IgG autoantibodies. Preferred diseases to detect include atopic asthma and non-atopic asthma. The invention also includes methods to prescribe and monitor treatment for animals with such diseases. Also included are kits to detect disease as well as kits to prescribe or monitor treatment. The present invention also includes formulations to treat chronic pulmonary diseases of the airways associated with anti-Fc$_\epsilon$R IgG autoantibodies. Preferred formulations include compounds that inhibit the ability of anti-Fc$_\epsilon$R IgG autoantibodies in susceptible animals to bind to Fc$_\epsilon$R-expressing cells. Also included are methods to treat such diseases.

5 Claims, No Drawings

DETECTION OF ANTI-FC$_\epsilon$R AUTOANTIBODIES IN ASTHMATICS

REFERENCE TO RELATED APPLICATION

This application claims priority from U.S. Provisional Application Serial No. 60/032,693, filed Dec. 10, 1996.

FIELD OF THE INVENTION

The present invention relates to the detection of anti-Fc epsilon receptor autoantibodies in animals having asthma and related chronic pulmonary diseases of the airways. The present invention also includes methods to treat such animals using compounds that inhibit the interaction between such autoantibodies and Fc epsilon receptors.

DESCRIPTION OF THE INVENTION

The present invention is based on the surprising discovery of anti-Fc$_\epsilon$R IgG autoantibodies in the serum of at least some asthmatic patients. The inventor believes this to be the first reporting of such autoantibodies associated with a chronic obstructive pulmonary disease of the airways.

The present invention includes methods to detect or treat a chronic obstructive pulmonary disease (COPD) of the airways associated with anti-Fc$_\epsilon$R IgG autoantibodies. As used herein, a chronic obstructive pulmonary disease of the airways refers to a disease that includes airway obstruction caused by infiltration of inflammatory cells, scarring, edema, smooth muscle hypertrophy/hyperplasia, smooth muscle contraction, and/or narrowing due to secretions (e.g., mucous) by cells. As used herein, anti-Fc$_\epsilon$R IgG autoantibodies refer to IgG antibodies produced by an animal against the animal's own high affinity Fc epsilon receptor RI (i.e., Fc$_\epsilon$R). A disease associated with such autoantibodies refers to a disease in which histamine release, as well as other functions of a Fc$_\epsilon$R-expressing cell, is apparently triggered by binding of such autoantibodies to the Fc$_\epsilon$Rs on those cell types (e.g., basophils, mast cells). Preferred chronic diseases to detect or treat include atopic asthma and non-atopic asthma, with non-atopic intrinsic asthma being more preferred. It is to be noted that inflammation is a major factor in the development and maintenance of asthma. In atopic asthma, allergens are thought to initiate the inflammatory process by triggering pulmonary mast cells (and other FcεR-expressing effector cells) in a type I (IgE-mediated) immediate allergic response, although it is possible that even atopic asthma has non-atopic components. In non-atopic intrinsic asthma (NAA) where there is no evidence for an allergic factor initiating the disease, the mechanisms that initiate inflammation have been less well understood. The inventor has discovered that at least a subset of patients with NAA has autoantibodies directed against the alpha ($\alpha$) chain of the high affinity IgE receptor FCeR expressed on mast cells. Furthermore, these autoantibodies are capable of activating ex vivo human basophils isolated from normal individuals. Therefore, these autoantibodies define a triggering, or activating, mechanism for the intrinsic asthma symptoms.

One embodiment of the present invention is a method to detect a COPD of the airways that includes the step of detecting anti-Fc$_\epsilon$R IgG autoantibodies in a bodily fluid collected from an animal susceptible to such a disease (e.g., an animal having such autoantibodies). A bodily fluid can include any fluid collectible from an animal such as, but not limited to, blood, serum, plasma, urine, tears, saliva, lymph, nasal secretions, milk, lung secretions, bronchoalveolar lavage fluid, feces, and other mucosal secretions. An animal susceptible to such a disease is any animal that can acquire the disease, and as such, has anti-Fc$_\epsilon$R autoantibodies. Preferred animals to detect include mammals, with humans, cats, dogs, horses, other pet animals, food animals, work animals, and zoo animals, being particularly preferred.

In one embodiment, anti-Fc$_\epsilon$R IgG autoantibodies can be detected by a method that includes the steps of (a) inactivating IgE in a collected bodily fluid to produce an IgE-deficient bodily fluid (i.e., a fluid containing essentially no IgE capable of binding to a Fc$_\epsilon$R); (b) contacting the IgE-deficient bodily fluid with a Fc$_\epsilon$R molecule under conditions suitable for the formation of a complex between the Fc$_\epsilon$R molecule and an anti-Fc$_\epsilon$R IgG autoantibody in the fluid; and (c) determining the presence of anti-Fc$_\epsilon$R IgG autoantibody by detecting the complex. Presence of the complex indicates the presence of anti-Fc$_\epsilon$R IgG autoantibody in the animal. IgE can be inactivated using methods known to those skilled in the art, such as heat treatment or removal or disabling of IgE using anti-IgE antibodies. An IgE-deficient fluid can also be produced by affinity chromatography to collect a fraction enriched for IgG. Methods to determine the presence of a complex are known to those skilled in the art, examples of which are disclosed herein.

As used herein, a Fc$_\epsilon$R molecule refers to any high affinity Fc$_\epsilon$RI, or a portion thereof, such that the portion retains the ability to bind to the Fc region of an IgE antibody. As such, a Fc$_\epsilon$R molecule can be an entire receptor, which can either be isolated from, or expressed on, a cell. In another, preferred, embodiment, a Fc$_\epsilon$R molecule is a Fc$_\epsilon$R $\alpha$ chain, with a Fc$_\epsilon$R soluble $\alpha$ chain (i.e., the extracellular domain of the $\alpha$ chain) being even more preferred.

An Fc$_\epsilon$R molecule of the present invention can include chimeric molecules comprising a portion of an Fc$_\epsilon$R molecule that binds to an IgE and a second molecule that enables the chimeric molecule to be bound to a substrate in such a manner that the Fc$_\epsilon$R portion binds to anti-Fc$_\epsilon$R IgG autoantibodies in essentially the same manner as a Fc$_\epsilon$R molecule that is not bound to a substrate. An example of a suitable second molecule includes a poly-histidine segment, preferably a poly-histidine segment comprising about six histidines. Such chimeric molecules can be produced using standard methods in the art, including but not limited to recombinant DNA technology.

In another embodiment, anti-Fc$_\epsilon$R autoantibodies are detected by a method that includes the steps of (a) inactivating any IgE in the IgG fraction to produce an IgE-deficient IgG fraction; (b) contacting the IgE-deficient IgG fraction with basophils or other Fc$_\epsilon$R-expressing cell types; and (c) determining if the IgE-deficient IgG fraction is capable of releasing histamine from the basophils. Histamine release indicates that the bodily fluid contains anti-Fc$_\epsilon$R IgG autoantibodies. Examples of these methods are disclosed herein. It is be noted that there are also a variety of other methods to detect autoantibodies known to those skilled in the art. An IgG fraction can be produced from the bodily fluid (methods to produce such a fraction include, but are not limited to Protein A or Protein G chromatography), prior to step (a).

The present invention also includes a kit to detect a COPD of the airways associated with anti-Fc$_\epsilon$R IgG autoantibodies. Such a kit includes a means to detect such autoantibodies. An example of such a means is a Fc$_\epsilon$R molecule, such as a Fc$_\epsilon$R $\alpha$ chain. Another example of such a means is a cell that expresses Fc$_\epsilon$R on its cell surface, such as a basophil or a cell transfected with a nucleic acid molecule that encodes a Fc$_\epsilon$R molecule. Examples of methods to use such kits are disclosed herein.

The present invention also includes a method to prescribe treatment for a COPD of the airways, in that the present invention teaches methods to identify a COPD associated with anti-Fc$_\epsilon$R IgG autoantibodies. Furthermore, the present invention includes a method to monitor the efficacy (e.g., success) of a treatment for a COPD of the airways, by determining the presence of complexes between anti-Fc$_\epsilon$R IgG autoantibodies and Fc$_\epsilon$Rs (i.e., anti-Fc$_\epsilon$R IgG autoantibody:Fc$_\epsilon$R complexes) in an animal. Also included in the present invention are kits to prescribe or monitor such treatments.

The present invention also includes a method to protect an animal from a COPD of the airways associated with anti-Fc$_\epsilon$R IgG autoantibodies. Such a method includes the step of inhibiting the binding of such an autoantibody to a Fc$_\epsilon$R-expressing cell in the animal. The ability to inhibit binding can be measured in a variety of ways, including measuring the ability of such autoantibodies to effect (i.e., trigger) histamine release by a Fc$_\epsilon$R-expressing cell. Suitable and preferred animals to treat are as identified as suitable and preferred animals in which to detect an anti-Fc$_\epsilon$R autoantibody associated COPD. A preferred method of treatment includes the step of administering to an animal an inhibitory compound that selectively binds to an anti-Fc$_\epsilon$R IgG autoantibody in a COPD patient, thereby preventing (i.e., inhibiting) the autoantibody from binding to a Fc$_\epsilon$R-expressing cell and, thus, inhibiting histamine release. A preferred inhibitory compound is a peptidometic compound that inhibits formation of a Fc$_\epsilon$R:anti-Fc$_\epsilon$R IgG autoantibody complex. Such a compound can be functionally and/or structurally similar to the natural substrate (e.g., either to the Fc$_\epsilon$R binding portion of the autoantibody or to the antibody-binding portion of the Fc$_\epsilon$R) such that the compound interferes with normal binding between the two natural substrates.

Also included in the present invention is a formulation to protect an animal from a COPD of the airways associated with anti-Fc$_\epsilon$R IgG autoantibodies. Such a formulation includes a compound that inhibits the ability of such autoantibodies to effect histamine release. Such a formulation can also include a pharmaceutically acceptable excipient (i.e., a composition that the animal can tolerate). A formulation can also include a pharmaceutically acceptable carrier, such as a controlled release formulation. Examples of carriers include, but are not limited to, biocompatible polymers, other polymeric matrices, capsules, microcapsules, microparticles, bolus preparations, osmotic pumps, diffusion devices, liposomes, lipospheres, and transdermal delivery systems. A formulation of the present invention can also include other compositions useful in the treatment of a COPD of the airways.

The present invention also includes an inhibitory compound identified by the compound's ability to selectively bind to an anti-Fc$_\epsilon$R IgG autoantibody in an animal susceptible to non-atopic intrinsic asthma associated with anti-Fc$_\epsilon$R IgG autoantibodies; such selective binding between the inhibitory compound and the autoantibody inhibits the autoantibody from binding to a Fc$_\epsilon$R-expressing cell and effecting histamine release from the cell. Such an inhibitory compound can, but need not, be identified by the following method: (a) contacting an anti-Fc$_\epsilon$R IgG autoantibody isolated from an animal susceptible to non-atopic intrinsic asthma with a putative inhibitory compound under conditions in which, in the absence of the compound, the autoantibody effects histamine release by a basophil; and (b) determining if the putative inhibitory compound inhibits the ability of the autoantibody to effect histamine release by the basophil.

The present invention also includes a test kit to identify a compound capable of inhibiting the ability of an anti-Fc$_\epsilon$R IgG autoantibody in an animal susceptible to non-atopic intrinsic asthma to effect histamine release. Such a test kit includes an anti-Fc$_\epsilon$R IgG autoantibody isolated from such an animal and a means for determining the extent of inhibition of histamine release activity in the presence of a putative inhibitory compound. Such means are known to those skilled in the art.

The following examples are provided for the purposes of illustration and are not intended to limit the scope of the present invention.

EXAMPLES

It is to be noted that the Examples include a number of molecular biology, microbiology, immunology and biochemistry techniques considered to be known to those skilled in the art. Disclosure of such techniques can be found, for example, in Sambrook et al., *Molecular Cloning: A Laboratory Manual,* Cold Spring Harbor Labs Press, 1989; and related references. Sambrook et al., ibid., is incorporated by reference herein in its entirety.

Example 1

This Example describes a method to detect anti-Fc$_\epsilon$R IgG autoantibodies in sera collected from non-atopic intrinsic asthma (NAA) patients.

The detection of anti-Fc$_\epsilon$R (i.e., anti-Fc$_\epsilon$R $\alpha$) IgG autoantibodies was performed as follows. IgG fractions were prepared from sera samples collected from ten NAA patients by affinity chromatography using protein G columns. In order to selectively denature IgE, the IgG fractions were heated for 3 hr at 56° to produce IgE-deficient IgG fractions; the inventor has verified that this established procedure effectively inactivated IgE but did not decrease IgG-mediated anti-Fc$_\epsilon$R reactivity.

The fractions were tested by western blot analysis against Fc$_\epsilon$R soluble-$\alpha$ chain blotted onto a membrane. Fc$_\epsilon$R soluble $\alpha$ chain was produced from cell culture supernatant of *Spodoptera frugiperda* Sf9 insect cells infected with a recombinant baculovirus vector expressing the extracellular portion of the huma Fc$_\epsilon$R $\alpha$ chain (i.e., nucleotides from about 88 through about 697 of the published sequence, Genbank accession number X06948; see also, Blank et al., 1991, *E. J. Biol. Chem.* 266, 2639–2646) and purified over an affinity column of anti-human $\alpha$ mAb 15-1 antibody, prepared in the laboratory of Dr. Jean-Pierre Kinet, Harvard University (see also Wang et al, 1992, *J. Exp. Med.* 175, 1353–1365; and Letourneur et al, 1995, *J. Biol. Chem.* 270, 8249–8256). The purified material migrated as a broad band around 35 kilodaltons (kD) when submitted to sodium dodecyl sulfate polyacrylamide gel electrophoresis (SDS PAGE). This broad band was due to the high degree of and heterogeneity in glycosylation. For western blot analysis, Fc$_\epsilon$R soluble $\alpha$ chain was submitted to SDS PAGE and transferred to an Immobilon membrane. The membrane was cut into strips, and each strip was incubated with a 1/10 dilution of an IgE-deficient IgG fraction prepared from each of the 10 collected sera. IgG binding to membrane strips was detected by incubation with an anti-human IgG antibody coupled to horse radish peroxidase (HRPO), followed by incubation with a chemiluminescent HRPO substrate (ECL system, available from Amersham; see also Scharenberg et al., 1995, *EMBO J.* 14, 3385–3394); the anti-human IgG antibody was verified not to cross-react with IgE. As a positive control for Fc$_\epsilon$R soluble $\alpha$ chain, one strip was incubated with the anti-human α mAb 19-1 antibody, which recognizes denatured α chain (see, for example, Blank et al. ibid., and Wang et al. ibid.), and detected with an anti-mouse IgG antibody conjugated to HRPO. As a negative control, incubation with serum was omitted. The specificity of the reactivity of positive sera was demonstrated on the absence of reactivity when these sera were preincubated with an excess of soluble α.

Of the ten NAA patients, the IgG fractions of four contained detectable amounts of anti-Fc$_\epsilon$R IgG autoantibodies (denoted NAA+ patients), whereas six did not (denoted NAA– patients). The six negative samples may be negative due to detection sensitivities of the assay or may not contain such autoantibodies.

Example 2

This Example demonstrates the ability of sera collected from NAA patients to stimulate histamine release from basophils.

The ability of the IgG fractions from the four NAA+ patients and six NAA– patients described in Example 1, as well as of IgG fractions produced from the sera of twelve normal individuals, to induce histamine release in normal basophils was tested. Basophils were semi-purified from the blood of two healthy donors by dextran sedimentation to produce basophil-enriched cell fractions. In vivo bound IgE that could have been present at the surface of these basophils was removed by acid treatment. Acid-treated basophil-enriched cell fractions were incubated for 40 min. at 37° C. in buffer containing interleukin 3 (IL-3) and a 1/5 dilution of an aliquot of NAA+, NAA–, or normal IgG fractions described above. Since each experiment was done with basophils from a different donor, release after triggering with the anti-α mAb 15-1 (described in Example 1) was used as a positive control in each experiment. The use of basophils from different donors resulted in the positive control release varying from 25 to 59% of the total histamine content. Therefore, to compare different experiments results were expressed as percentage of the positive control within each experiment.

The results are presented in Table 1.

|  | Number of Patients | Histamine Release (% of positive control) | | |
| --- | --- | --- | --- | --- |
|  |  | Mean | Variance | Std. Err. |
| NAA+ | 4 | 33.000 | 810.000 | 14.230 |
| NAA– | 6 | 16.167 | 117.367 | 4.423 |
| N | 10 | 9.950 | 96.136 | 3.101 |

NAA+ denote NAA patients who have anti-Fc$_\epsilon$R IgG autoantibodies, per the assay described in Example 1; NAA– denotes patients who do not have anti-Fc$_\epsilon$R IgG autoantibodies, per the assay described in Example 1; N are normal individuals. The number of individuals in each category is indicated, as is the mean, variance and standard error for each group. A t test gave the following values for p: NAA+ versus NAA–, p=0.2162; NAA+ versus normals, p=0.0366; NAA– versus normals, p=0.2569. These results indicate that sera collected from NAA+ patients apparently can induce histamine release in basophils. There is even some suggestion that sera collected from NAA– patients may have some histamine releasing activity.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method to detect non-atopic intrinsic asthma associated with anti-Fc$_\epsilon$RI IgG autoantibodies, said method comprising detecting anti-Fc$_\epsilon$RI IgG autoantibodies in the bodily fluid of an animal.

2. The method of claim 1 wherein said method comprises:

(a) inactivating IgE in said bodily fluid to produce an IgE-deficient bodily fluid;

(b) contacting said IgE-deficient bodily fluid with a Fc$_\epsilon$RI molecule under conditions suitable for the formation of a complex between said Fc$_\epsilon$RI molecule and an anti-Fc$_\epsilon$RI IgG autoantibody in said fluid; and (c) determining the presence of said anti Fc$_\epsilon$RI IgG autoantibody by detecting said complex, the presence of said complex indicating the presence of said anti-Fc$_\epsilon$RI IgG autoantibody in said animal.

3. The method of claim 2, wherein said Fc$_\epsilon$RI molecule comprises a Fc$_\epsilon$RI α chain.

4. The method of claim 1, wherein said method comprises:

(a) producing an IgG fraction from said bodily fluid;

(b) inactivating any IgE in said IgG fraction to produce an IgE-deficient IgG fraction;

(c) contacting said IgE-deficient IgG fraction with basophils; and (d) determining if said IgE deficient IgG fraction is capable of releasing histamine from said basophils, wherein histamine release indicates that said bodily fluid contains anti-Fc$_\epsilon$RI IgG autoantibodies.

5. A method for prescribing treatment for non-atopic intrinsic asthma, said method comprising: (a) determining the presence of anti-Fc$_\epsilon$RI IgG autoantibodies in an animal, wherein presence of anti-Fc$_\epsilon$RI IgG autoantibodies indicates the presence of non-atopic intrinsic asthma; and (b) prescribing a treatment for non-atopic intrinsic asthma as identified in step (a).

* * * * *